United States Patent [19]

Peng

[11] 4,131,115

[45] Dec. 26, 1978

[54] EYELIDS-TURNING AND EYE-WASHING FIXTURE

[76] Inventor: Sung S. Peng, No. 46 Lane 31, Alley 81, Sec. 2, Taipei, Taiwan

[21] Appl. No.: 842,969

[22] Filed: Oct. 17, 1977

Related U.S. Application Data

[63] Continuation of Ser. No. 724,773, Sep. 20, 1976, abandoned.

[51] Int. Cl.[2] ................................................ A61M 7/00

[52] U.S. Cl. ...................................................... 128/249

[58] Field of Search ................................ 128/248, 249

[56] References Cited

U.S. PATENT DOCUMENTS

| | | | |
|---|---|---|---|
| 1,362,682 | 12/1920 | Dayton | 128/249 |
| 2,524,720 | 10/1950 | Watros | 128/249 |
| 2,589,178 | 3/1952 | Wintle, Jr. | 128/249 |

FOREIGN PATENT DOCUMENTS

| | | | |
|---|---|---|---|
| 295162 | 11/1914 | Fed. Rep. of Germany | 128/249 |

*Primary Examiner*—John D. Yasko

*Attorney, Agent, or Firm*—Holman & Stern

[57] ABSTRACT

A combined fixture for turning the eyelids and washing the eye is disclosed. This apparatus utilizes one bottle to contain the clean water and dirty water in separate parts. A pair of blades is attached with the bottle that can be utilized to clip the upper eyelid outwardly. A roller set which can be turned just into one direction enables the clipped upper eyelid to be turned inside out. By means of a air chamber, the clean water in the bottle can be flowed to spray into a washing basin which attaches together with the bottle as a whole body to wash the eye and eyelids. The lower eyelid is clipped by another element. A hole with a valve is opened on the bottle which enables the repeated pressing of the air chamber to flow the clean water to spray into the washing basin in continuously condition, not in the intermittent condition. The water after it is utilized will flow back into another part of the bottle and then be drained out. So that all the process of turning the eyelids inside out and washing the eye is completed without make the hand touching the eyelids. The strict sanitary principle can be kept therefore.

4 Claims, 5 Drawing Figures

EYELIDS-TURNING AND EYE-WASHING FIXTURE

This is a continuation of application Ser. No. 724,773, filed Sept. 20, 1976 now abandoned.

BRIEF SUMMARY OF THE INVENTION

This invention relates to a combined apparatus and is specifically concerned with the provision of an eyelids-turning and eye-washing fixture.

The eye is the important sensing organ of the human body. The eye hygiene is an important work to everyone. The conventional eye-washing fixtures are so simple that many shortcomings can not be avoided at all. For example, the utilized dirty water will flow back into the bottle again, so that the mixture of the clean water with the dirty water in the conventional fixtures makes the eye-washing effect decrease again and again. Meanwhile, the eye-turning processes are completed by hand in the conventional eye-washing method. Hence, the strict sanitary principle can not be kept.

It is a primary objective of the instant invention to provide a fixture which does not exhibit the disadvantage of known construction and which is both convenient and sanitary to use.

The objectives are implemented by the subject invention which combines a bottle to contain the clean water and dirty water in its separate parts with a clip and a roller set. The clip can pull the upper eyelid outwardly and the roller set will turn the eyelid inside out. The repeated pressing of an air chamber which attaches to the bottle as a whole body will cause flow of the clean water to spray into a washing basin to wash the eye in continuously condition. Therefore the eyelid can be turned inside out and the eye can be washed by the absolutely clean water, but without the use of a hand to touch the eye in all these processes.

DETAILED DESCRIPTION

Figure 4:
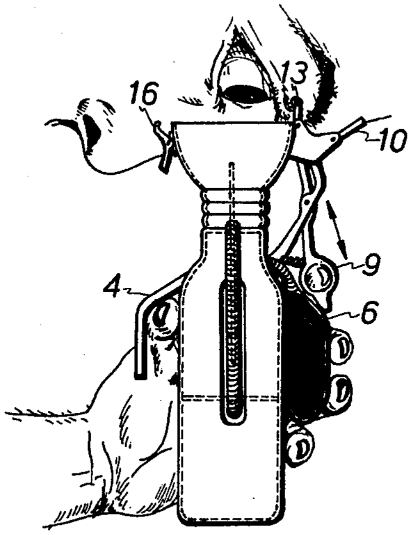
FIG. 4 illustrates the usage of this invention, while the upper eyelid is clipped.
Figure 5:
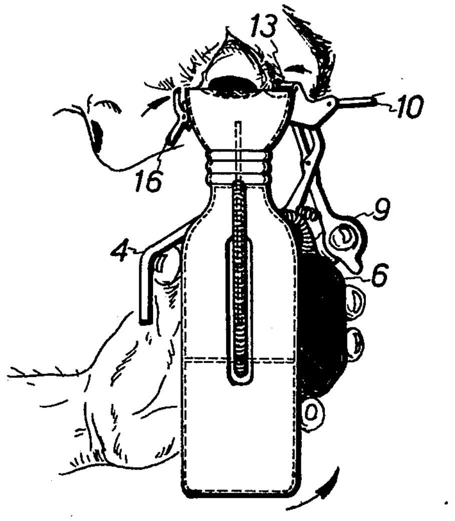
FIG. 5 illustrates the usage of this invention, while the lower eyelid is clipped and the upper eyelid is turned inside out.

Now with reference to the drawings, this invention will be seen to consist of three major parts, the eyelids-turning element, and eye-washing element, and a bottle. The bottle is divided into the clean water container 1 and dirty water container 2. The cork 3 stuffs a hole through which the clean water will be poured into the container 1. At using this invention, one have to put his thumb against the holder 4 and have his index finger entering into the hoop 5. His other finger can compress the air chamber 6. Along the groove 7 of seat 8, the clip 9 will be controlled by the index finger to move upwardly to touch the upper eyelid. Then, as shown in FIG. 4, the upper eyelid will be clipped by the clip 9. The image of the upper eyelid on the mirror 10, which is installed at front of seat 8, can be seen clearly.

By means of a spring 11 of the slider 12, the upper eyelid is pulled outwardly. Meanwhile the roller set 13 touches against the upper end of this eyelid. Then, turning this invention forward enables the support 14, together with the roller 15 installed on it, to reverse back to turn the upper eyelid, which is clipped by the clip 9, inside out. The lower eyelid is clipped by the clip 16.

Pressing the air chamber 6 will flow the clean water in container 1 to pass through the nozzle 17 to spray out, so that the eye will be washed. After having washed the eye, the dirty water flows through the hole 18 and pipe 19 back to the container 2 and will be drained out from the exit 20.

The air chamber 6 is made of the elastic material, so it will rebound immediately after being pressed. An air hole 21 with a valve 22 is opened just beyond the pipe 23 of air chamber 6. By means of a spring, the valve 22 opens the air hole 21 while the air chamber 6 is not being pressed. As soon as the air chamber 6 is pressed, the valve 22 closes the air hole 21 immediately. Hence the successive opening and closing of the air hole 21 will enable the water to be flowed to spray out in the continuously condition, but not in the intermittent condition.

Figure 1:
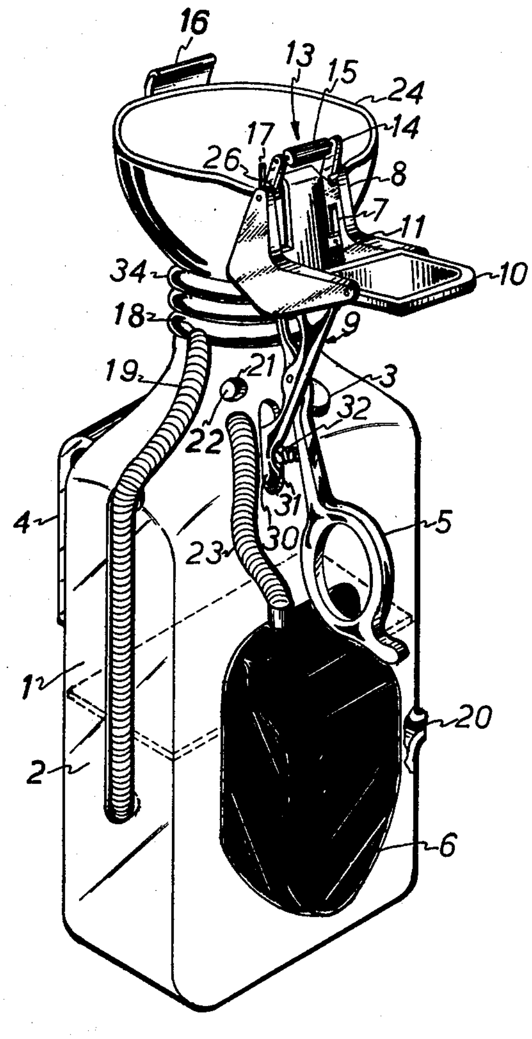
FIG. 1 is a schematic illustration depicting the structure of this invention.
Figures 2, 3:
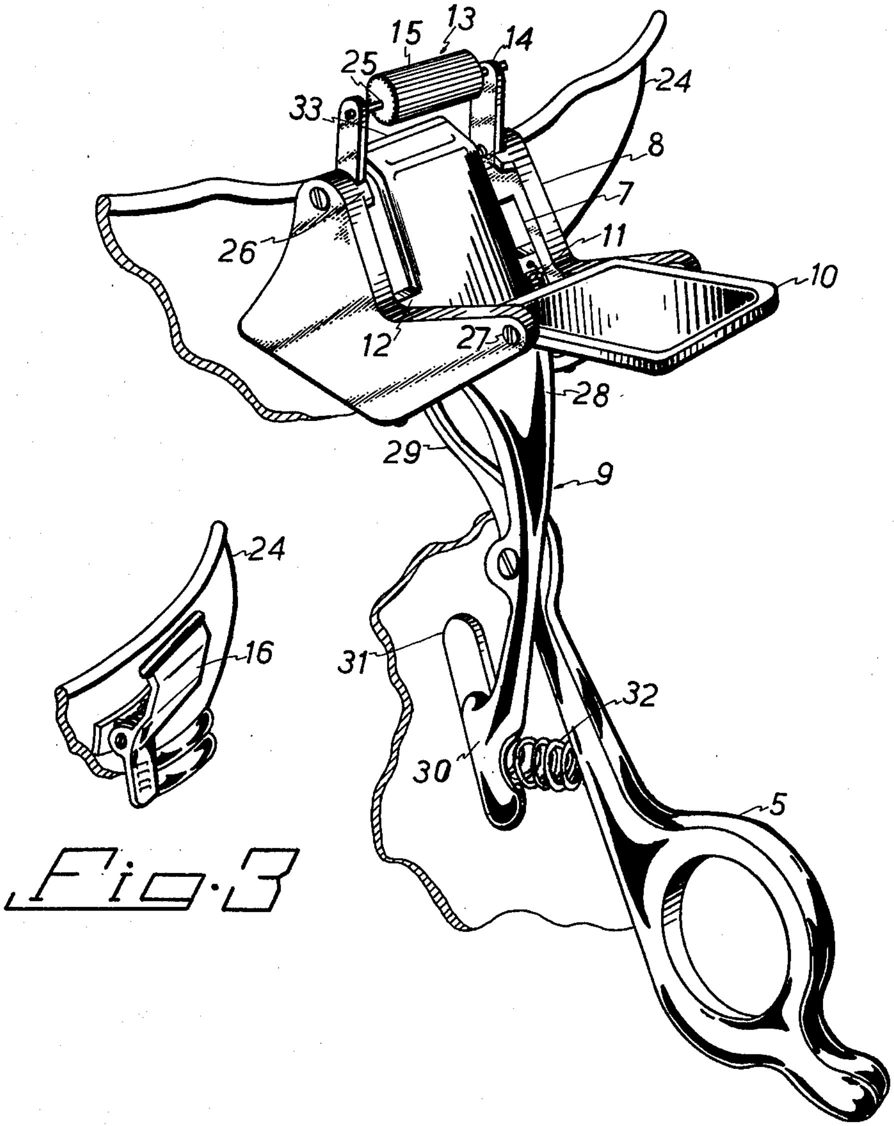
FIG. 2 is a pictorial illustration of the clip and roller set of this invention.
FIG. 3 is a pictorial illustration of the clip for the lower eyelid.

As shown in FIG. 2, the eyelids-turning element of instant invention comprises a seat 8 in front of washing basin 24, and a roller set 13 which includes a roller 15 made of elastic material and an axle 25 installed at the support 14 of seat 8. The bar 26 of seat 8 is utilized in order to limit the turning direction of support 14. At inside of the seat 8, two grooves 7 are utilized to guide the movement of clip 9, by means of slider 12 and spring 11. The axle 27 of mirror 10 is installed at the seat 8 also.

The clip 9 comprises of two blades 28 and 29 which are pivoted together. One end 30 of blade 28 is inserted into the hole 31. One spring 32 connects the end 30 of blade 28 with the blade 29 just beyond the hoop 5. The upper ends of both blade 28 and 29 have a soft material layer 33 in order to avoid any harm to the delicate upper eyelid. The lower eyelid clip 16 is installed on the washing basin 24 on the opposite side from the seat 8. By means of the spring function, the lower eyelid can be clipped by 16.

A flexible pipe 34 is utilized to connect the washing basin 24 and the bottle. So that any position and direction of the bottle can be regulated at washing the eye.

I claim:

1. An eyelid-turning and eye-washing fixture comprising:
   - a bottle which is divided into a clean water container and a dirty water container;
   - a washing basin connected with said bottle;
   - spray means interconnecting said clean water container with said washing basin for causing the clean water in said container to spray out in said washing basin;
   - means for clipping and turning an eyelid affixed to said bottle and said washing basin.

2. The fixture of claim 1 where said means for clipping and turning an eyelid comprises clipping means slidably mounted on said washing basin, and means formed in a scissor arrangement for operating said clipping means mounted on said bottle.

3. The fixture of claim 2 wherein said means for clipping and turning an eyelid further comprises roller means secured to said washing basin operatively associated with said clipping means for rolling said eyelid when the same is clipped.

4. An eyelid-turning and eye-washing fixture comprising: a bottle which is divided into the clean water container and dirty water container;

a washing basin which, by means of a flexible pipe, connects with said bottle;

an air chamber attached together with said bottle for causing the clean water in said container to spray out in said washing basin; a hole with a valve just beyond the pipe connecting said air chamber with said bottle can be adapted with the pressing of said air chamber to be opened or closed, so that the clean water in said container flows into said washing basin in a continuously condition, not in an intermittent condition;

a clip which includes two blades pivoted together and connected with each other by a spring; one end of first said blade inserts into a hole in said bottle, its other end is flatted with two protuberant sliders and with a soft material layer at its utmost front end to avoid any harm to the upper eyelid can be caused; one end of second blade has a hoop which is manipulated by the index finger, the other end of this blade has a soft material layer also;

a roller set, which is installed on said washing basin and utilized as the upper eyelid-turning element, including a seat attached together with said bottle, a pivoted roller and a pivoted mirror which can reflect the image of the eye so that it will be seen clearly by the user, and a bar which can limit the turning direction of the support of said roller; a lower eyelid clip attached on said washing basin at the opposite position against said roller set;

a holder attached on said bottle to be pushed by the thumb during use;

a flexible pipe connecting said washing basin and said dirty water container so that it enables the dirty water to flow back into said dirty water container and to be drained out through a hole opened in it;

said pair of blades can clip the upper eyelid outwardly and said roller set can can turn the upper eyelid inside out when the said bottle is moved forward, and pressing said air chamber by hand will cause the clean water to be sprayed into said washing basin to wash the eye.

* * * * *